(12) United States Patent
Cooperwood

(10) Patent No.: US 7,687,486 B2
(45) Date of Patent: Mar. 30, 2010

(54) SELECTIVE ESTROGEN RECEPTOR MODULATORS

(75) Inventor: John S. Cooperwood, Tallahassee, FL (US)

(73) Assignee: Florida Agricultural & Mechanical University, Tallahassee, FL (US)

( * ) Notice: Subject to any disclaimer, the term of this patent is extended or adjusted under 35 U.S.C. 154(b) by 939 days.

(21) Appl. No.: 11/073,087

(22) Filed: Mar. 5, 2005

(65) Prior Publication Data

US 2005/0182038 A1    Aug. 18, 2005

Related U.S. Application Data

(63) Continuation-in-part of application No. 10/835,312, filed on Apr. 28, 2004, now abandoned.

(60) Provisional application No. 60/466,521, filed on Apr. 29, 2003.

(51) Int. Cl.
*A61K 31/58* (2006.01)
*A61K 31/56* (2006.01)
*C07J 1/00* (2006.01)
*C07J 43/00* (2006.01)

(52) U.S. Cl. .................. 514/176; 514/178; 514/182; 540/107; 540/108; 552/626

(58) Field of Classification Search .............. 552/626; 540/107, 108; 514/176, 178, 182
See application file for complete search history.

(56) References Cited

U.S. PATENT DOCUMENTS 3,212,971 A * 10/1965 Allais et al. ............. 514/176
3,214,446 A * 10/1965 Evans et al. .............. 552/626
3,519,714 A    7/1970 Hughes et al.
5,554,604 A    9/1996 Bonfils et al.
5,580,864 A   12/1996 Bonfils et al.
5,635,498 A    6/1997 Bonfils et al.
5,672,595 A    9/1997 Bonfils et al.
5,739,124 A    4/1998 Bonfils et al.

FOREIGN PATENT DOCUMENTS

GB        1045657      * 10/1966

OTHER PUBLICATIONS

Journal of Pharmacy and Pharmacology, The Pharmaceutical Society of Great Britain, vol. 16, No. 2, D.D. Evans et al., pp. 717-724, 1964.
Chemical Abstracts vol. 58, 13012, 1963.

* cited by examiner

*Primary Examiner*—Barbara P Badio
(74) *Attorney, Agent, or Firm*—Robert Thompson

(57) ABSTRACT

Compositions and methods for treating a cancer in mammals by administering selective estrogen receptor modulators particularly compounds represented by:

Structure I $$R_1R_2N-(CH_2)_n-O-\text{[steroid core with } R_3, R_4, R_5, R_6, R_7\text{]}$$

or any other of the structures contained herein, or of a stereoisomer, enantiomer, rotomer, tautomer or pharmaceutically acceptable salt form thereof.

31 Claims, No Drawings

SELECTIVE ESTROGEN RECEPTOR MODULATORS

CROSS REFERENCE TO CO-PENDING APPLICATION

This is a continuation-in-part of U.S. patent application Ser. No. 10/835,312 now abandoned, filed in the name of John S. Cooperwood on Apr. 28, 2004 which claims the benefit of provisional patent application No. 60/466,521 filed Apr. 29, 2003. The entire disclosures of which are incorporated herein by reference in their entirety.

GOVERNMENTAL INTEREST

This invention was supported with United States government funding through the National Institutes of Health Grant No. RR0320-18-ARC.

BACKGROUND

The present invention relates to compounds that have biological activity with respect to estrogen receptors. The invention also relates to the use of such compounds to treat diseases and disorders related to estrogen receptor activity. More particularly, the present invention provides selective estrogen receptor modulators ("SERMs") for use, for example, in treating mammalian cancers. The present invention therefore relates to the fields of medicine, medicinal chemistry, biochemistry, and endocrinology.

Estrogen is a hormone critical to normal human development and function. Although estrogen is the predominant "sex hormone" in women, in whom estrogen controls the development of female sex characteristics and the development and function of the reproductive system (Berkow, Beers et al. 1997), it is also found in men (Gustafsson 1998). Women produce estrogen primarily in the ovaries; however, estrogen affects a variety of physiological functions in women including body temperature regulation, maintenance of the vaginal lining, and preservation of bone density (Jordan 1998). In addition, estrogen provides additional effects that are related to its ability to modulate production of cholesterol in the liver, as demonstrated by the reduced occurrence of atherosclerosis in women compared to men due in part to the reduction of low-density lipoprotein ("LDL") (Jordan 1998). Estrogen has also been implicated in delaying and/or reducing the severity of Alzheimer's Disease (Jordan 1998).

Failure to produce estrogen has profound physiological consequences in females. Failure to produce estrogen resulting from incomplete or absent ovary development (Turner's Syndrome) causes deficiencies in the skin, bone (e.g., severe osteoporosis), and other organs severely affecting the life of the afflicted individual (Dodge 1995). In normal women, estrogen production falls sharply upon the onset of menopause, usually at about 50 years of age. The effects of the loss of estrogen production include increased atherosclerotic deposits (leading to an increased incidence of heart disease), decreased bone density (osteoporosis), and fluctuations in body temperature (Jordan 1998). Often, the effects of reduced estrogen production are addressed by hormone replacement therapy (Dodge 1995; Berkow, Beers et al. 1997; Jordan 1998).

However, estrogen also has some undesirable side effects. In menopausal women, supplementation of estrogen is associated with alleviation of the above-described unwanted indications. But, administration of estrogen is also associated with increased risks for breast and endometrial cancer as well as blood clots (Jordan 1998). The increased risk of endometrial cancer can be addressed by the administration of progesterone (or its synthetic analog progestin) to re-initiate menstruation and thereby shed potentially malignant cells, but many older women find this undesirable (Jordan 1998). Breast cancer, however, is by far the greater risk of estrogen replacement therapy, affecting one woman in every 15 between the ages of 60 and 79 (Jordan 1998).

Estrogen has also been shown to function as a mitogen in estrogen-receptor positive breast cancer cells. Thus, treatment regiments which include antiestrogens, synthetic compounds which oppose, the actions of estrogen have been effective clinically in halting or delaying the progression of the disease (Jordan and Murphy, Endocrine Reviews 11:578-610 1990); Parker, Breast Cancer Res. Treat. 26:131-137 (1993)). The availability of these synthetic estrogen receptor modulators and subsequent dissection of their mechanism(s) of action have provided useful insights into estrogen receptor action.

The human estrogen receptor is a member of the nuclear receptor superfamily of transcription factors (Evans, Science 240:889-895 (1988)). In the absence of the hormone, it resides in the nucleus of target cells in a transcriptionally inactive state. Upon binding ligand, the estrogen receptor undergoes a conformational change initiating a cascade of events leading ultimately to its association with specific regulatory regions within target genes (O'Malley et al., Hormone Research 47:1-26 (1991)). The ensuing effect on transcription is influenced by the cell and promoter context of the DNA-bound receptor (Tora et al. Cell 59:471-487 (1989) (Tasset et al., Cell 62:1177-1181 (1990); McDonnell et all Mol. Endocrinol. 9:659-669 (1995); Tzukerman et al. Mol. Endocrinol. 8:21-30 (1994)). It is in this manner that the physiological estrogen receptor-agonist, estradiol, exerts its biological activity in the reproductive, skeletal and cardiovascular systems (Clark and Peck, Female Sex Steroids: Receptors and Function (eds) Monographs Springer-Verlag, New York (1979); Chow et al., J. Clin. Invest. 89:74-78 (1992); Eaker et al. Circulation 88:1999-2009 (1993)).

Thus, for a long time the treatment options for the serious health problems caused by a failure to produce estrogen were limited and entailed severe risks. However, the discovery that some agents acted as estrogen agonists in some tissues (e.g., bone) and as an antagonists in other tissues (e.g., breast) provided hope that more effective treatments for estrogen loss could be found (Gradishar and Jordan 1997; Gustafsson 1998; Jordan 1998; MacGregor and Jordan 1998).

Currently, the SERM's consist of two main chemical classes: the triphenylethylene derivatives and benzothiophene derivatives. SERM's approved by the Food and Drug Administration (FDA) and used in the treatment of breast cancer, are tamoxifen and toremifene. Another SERM, raloxifene is currently approved by the FDA for osteoporosis. Tamoxifen has been associated with endometrial cancer due to its estrogenic activity within the uterus while raloxifene lacks estrogenic activity within the uterus. However, tamoxifen has been associated with endometrial cancer and venous blood clots (Jordan 1998; MacGregor and Jordan 1998). In addition, tumor resistance to tamoxifen can occur (MacGregor and Jordan 1998).

It is apparent that there is a need to find a SERM with antiestrogenic activity and minimal side effects.

The best known of these so-called Selective Estrogen Receptor Modulators ("SERMs"), tamoxifen, has been demonstrated to have therapeutic utility in treating and preventing breast cancer and lowering LDL concentrations; yet, without significant reduction in bone density (Jordan 1998; MacGregor and Jordan 1998).

Estrogen is thought to be involved in the triggering of breast cancer as well as other cancers due to improper or excessive signaling. Tamoxifen as well as other SERMs are believed to block this triggering affect of estrogen. Over the years, tamoxifen has become the agent of choice in the treatment of all stages of breast cancer. Tamoxifen has provided an effective treatment against Estrogen receptor positive breast cancers. Clinical trials have shown that tamoxifen, when used as an adjuvant therapy, can increase the survival rate of women with estrogen receptor positive tumors and in women whose estrogen receptor status is not known. Nevertheless, tamoxifen is associated with serious side effects, such as thromboembolic events, negative vasomotor symptoms, and an increased risk of endometrial cancer and cataracts.

Tamoxifen has been followed recently by newer SERMs, in particular raloxifene, that promise to provide many of tamoxifen's benefits with fewer risks (Howell, Downey et al. 1996; Gradishar and Jordan 1997; Gustafsson 1998; Jordan 1998; Purdie 1999; Sato, Grese et al. 1999). These newer SERMs, including idoxifene (Nuttall, Bradbeer et al. 1998), CP-336, 156 (Ke, Paralkar et al. 1998), GW5638 (Willson, Norris et al. 1997), LY353581 (Sato, Turner et al. 1998) are part of the second and third generation of partial estrogen agonists/antagonists. In addition, a new generation of pure antiestrogens such as RU 58,688 (Van de Velde, Nique et al. 1994) have been reported. A large number of additional partial and pure estrogen agonist/antagonist compounds and treatment modalities have reported (Bryant and Dodge 1995; Bryant and Dodge 1995; Cullinan 1995; Dodge 1995; Grese 1995; Labrie and Merand 1995; Labrie and Merand 1995; Thompson 1995; Audia and Neubauer 1996; Black, Bryant et al. 1996; Thompson 1996; Cullinan 1997; Wilson 1997; Miller, Collini et al. 1999; Palkowitz 1999; Wilson 1999).

One embodiment of the present invention comprises a method of using aminoalkyloxy derivatives of 1,3,5(10)-Estratrien steroids as selective estrogen receptor modulators in the treatment of mammalian cancers. These compounds consist of various aminoalkyloxy derivatives of 1,3,5(10)-Estratrien steroids and are used, for example, as agents in the treatment of cancer in mammals. Selective estrogen receptor modulators (SERMs) are comprised of a group of compounds that act as estrogen receptor agonists in some tissues and as estrogen receptor antagonists in others. SERMs may interact with receptors, for example, by diffusing into the cell and binding to estrogen receptor subunits, α or β. During this process, there is a conformational change to the receptors which results in dimerization. It is this dimerization of receptors that facilitates binding to the promoter regions on DNA. The conformational change of receptors, particularly the position of helix 12, dictates whether the SERM is agonist or antagonist causing activation or suppression of estrogen target genes.

Toremifene is another FDA approved SERM used in the treatment of advanced breast cancer in postmenopausal women. Toremifene's efficacy is very similar to that of tamoxifen against estrogen positive metastatic breast cancer. In a worldwide phase III multi-center clinical trial comparing toremifene with tamoxifen, results indicated that the two drugs had very similar response rates of 44% for tamoxifen, 20 mg/day, while the response rates for toremifene were 50% and 48% at 60 and 200 mg/day, respectively. These results indicated that both drugs have similar efficacy in treating advanced breast cancer. As with tamoxifen, toremifene has also been studied as an adjuvant therapy. In this multi-center clinical trial, toremifene was not found to exhibit a statistically significant reduction in the recurrence of breast cancer. Surprisingly, toremifene has been associated with fewer side effects in comparison with tamoxifen. This advantage may be pivotal in the approval by the FDA as an adjuvant therapeutic treatment for breast cancer. Raloxifene is a SERM approved by the FDA in treatment and prevention of osteoporosis. Raloxifene has estrogen antagonist activity in breast tissue. Unfortunately, preclincal studies indicated that it has no advantage over tamoxifen in treating postmenopausal women with advanced breast cancer. In an addition, raloxifene is not effective against tamoxifen resistant breast cancer. But it is still being considered as a prophylactic therapy against cancer in high-risk women. Based upon the in vitro studies, the aminoalkyloxy derivatives of 1,3,5(10)-Estratrien steroids are effective at inhibiting the growth of cancer cells. Particularly, these derivatives are effective at inhibiting the growth of breast cancer cells such as MCF-7 cells. These same compounds may be effective against endometrial cancer cells.

Embodiments of the present invention provide aminoalkyloxy estrogen receptor agonist and antagonist compounds in addition to methods and compositions for treating or preventing estrogen receptor-mediated disorders. The compounds described herein have been found to have unexpected and surprising activity in modulating estrogen receptor activity. Thus, the compounds of the present invention may have utility in preventing or treating estrogen receptor-mediated disorders such as, for example, breast cancer, osteoporosis, endometrial cancers, atherosclerosis, menopause, premenstrual syndrome and Alzheimer's disease.

In a first aspect, the present invention provides compounds having the structure represented by:

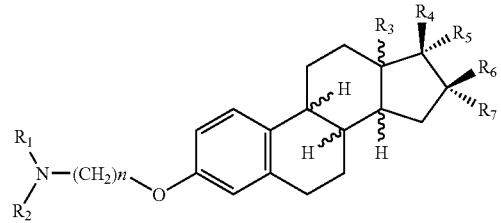

or a stereoisomer, enantiomer, rotomer, tautomer or a pharmaceutically acceptable salt thereof, wherein:

a) $R_1$ and $R_2$ are independently selected from the group consisting of hydrogen, alkyl having 1 to 8 carbon atoms, and nitrogen to form a saturated 5 to 6 ring heterocycle, b) $R_3$ is α or β methyl, c) n is an integer from 2 to 10, d) $R_4$ is selected from the group consisting of hydrogen, hydroxy, ethynyl, fluorine, chlorine, bromine, iodine and acyloxy of a organic carboxylic acid of from 1 to 10 carbon atoms or taken together with the nitrogen to form a saturated 5 to 6 ring heterocycle optionally containing a second nitrogen or oxygen in the ring, carboxylic acid alkyl, alkenyl and alkynyl of from 1 to 10 carbons, e) $R_5$ is selected from the group consisting of hydrogen, hydroxy, ethynyl, fluorine, chlorine, bromine, iodine and acyloxy of a organic carboxylic acid of from 1 to 10 carbon atoms or taken together with the nitrogen to form a saturated 5 to 6 ring heterocycle optionally containing a second nitrogen or oxygen in the ring, carboxylic acid alkyl, alkenyl and alkynyl of from 1 to 10 carbons, and f) $R_6$ and $R_7$ are independently selected from the group consisting of hydrogen, hydroxy, ethynyl, fluorine, chlorine, bromine, iodine and acyloxy of an organic carboxylic acid of from 1 to 10 carbons.

In yet another aspect, embodiments of the present invention provide methods for treating or preventing an estrogen receptor-mediated disorders in a mammalian subject in which an amount of an estrogen receptor-modulating compound of the invention that is effective to modulate estrogen receptor activity in the subject is administered. Other embodiments provide methods for treating a cell or an estrogen receptor-mediated disorder in a human or animal subject, comprising administering to the cell or to the human or animal subject an amount of a compound or composition of the invention embodiments effective to modulate estrogen receptor activity in the cell or subject. Representative estrogen receptor-mediated disorders include, for example, osteoporosis, atherosclerosis, estrogen-mediated cancers such as, for example, breast and endometrial cancer, and Alzheimer's disease.

These and other aspects and advantages will become apparent when the description below is read in conjunction with the accompanying examples and claims.

DESCRIPTION

Definitions

"Estrogen Receptor" as defined herein refers to any protein in the nuclear receptor gene family that binds estrogen, including, but not limited to, any isoforms or deletion mutations having the characteristics just described. More particularly, the present invention relates to estrogen receptor(s) for human and non-human mammals. Human estrogen receptors included in the present invention include the alpha and beta-isoforms (referred to herein as "estrogen receptor alpha." and "estrogen receptor beta.") in addition to any additional isoforms as recognized by those of skill in the biochemistry arts.

"Estrogen Receptor Modulator" refers herein to a compound that can act as an inhibitor estrogen receptor alpha enriched breast cancer cells having an $IC_{50}$ or $EC_{50}$ of no more than about 50 muM as determined using the estrogen receptor alpha enriched breast cancers proliferation assay described herein below. Representative compounds of the present invention have been discovered to exhibit antagonist activity via. estrogen receptor alpha enriched breast cancer cells. Compounds of the present invention specifically exhibit an antagonist $IC_{50}$ or $EC_{50}$ with respect to estrogen receptor alpha enriched breast cancer cells of no more than about 50.mu.M, "$IC_{50}$" is that concentration of inhibitor at which 50 percent of growth or inhibition of a target such as, for example, estrogen receptor alpha enriched breast cancer cells. The term "MCF-7 cells" as used herein relates to estrogen receptor alpha enriched breast cancer cells taken from patients.

A "Selective Estrogen Receptor Modulator" (or "SERM") is a compound that exhibits activity as an agonist or antagonist of an estrogen receptor (e.g., estrogen receptor alpha or estrogen receptor beta in a tissue-dependent manner. Thus, as will be apparent to those of skill in the biochemistry and endocrinology arts, compounds of the invention that function as SERMs can act as estrogen receptor agonists in some tissues such as, for example, bone, brain, and/or heart and as antagonists in other tissue types, such as, for example, the breast and/or the uterine lining.

"Optionally substituted" refers to the replacement of hydrogen with a monovalent or divalent radical. Suitable substitution groups include, for example, hydroxyl, nitro, amino, imino, cyano, halo, thio, thioamido, amidino, oxo, oximino oxamidino, methoxamidino, imidino, guanidino, sulfonamido, carboxyl, formyl, lower alkyl, halo lower alkyl, lower alkoxy, halo lower alkoxy, lower alkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like. The substitution group can itself be substituted. The group substituted onto the substitution group can be, for example, carboxyl, halo; nitro, amino, cyano, hydroxyl, lower alkyl, lower alkoxy, aminocarbonyl, —SR, thioamido, —$SO_3H$, —$SO_2R$ or cycloalkyl, where R is typically hydrogen, hydroxyl or lower alkyl. When the substituted substituent includes a straight chain group, the substitution can occur either within the chain (e.g., 2-hydroxypropyl, 2-aminobutyl, and the like) or at the chain terminus such as, for example, 2-hydroxyethyl, 3-cyanopropyl, and the like. Substituted substitutents can be straight chain, branched or cyclic arrangements of covalently bonded carbon or heteroatoms.

Alkyl, lower alkyl and Related Terms "Lower alkyl" as used herein refers to branched or straight chain alkyl groups comprising one to ten carbon atoms that independently are unsubstituted or substituted, e.g., with one or more halogen, hydroxyl or other groups. Examples of lower alkyl groups include, but are not limited to, methyl, ethyl, propyl, isopropyl, n-butyl, t-butyl, n-hexyl, neopentyl, trifluoromethyl, pentafluoroethyl, and the like.

"Alkylenyl" refers to a divalent straight chain or branched chain saturated aliphatic radical having from 1 to 20 carbon atoms. Typical alkylenyl groups employed in compounds of the present invention are lower alkylenyl groups that have from 1 to about 6 carbon atoms in their backbone. "Alkenyl" refers herein to straight chain, branched, or cyclic radicals having one or more double bonds and from 2 to 20 carbon atoms. "Alkynyl" refers herein to straight chain, branched, or cyclic radicals having one or more triple bonds and from 2 to 20 carbon atoms.

The term "lower haloalkyl" refers to a lower alkyl radical substituted with one or more halogen atoms.

"Lower alkoxy" as used herein refers to RO— wherein R is lower alkyl. Representative examples of lower alkoxy groups include methoxy, ethoxy, t-butoxy, trifluoromethoxy and the like.

"Lower alkylthio" as used herein refers to RS— wherein R is lower alkyl.

The term "alkoxyalkyl" refers to the group-$alk_1$-O-$alk_2$ where $alk_1$ is alkylenyl or alkenyl, and $alk_2$ is alkyl or alkenyl. The term "lower alkoxyalkyl" refers to an alkoxyalkyl where $alk_1$ is lower alkylenyl or lower alkenyl, and $alk_2$ is lower alkyl or lower alkenyl. The term "aryloxyalkyl" refers to the group -alkylenyl-O-aryl. The term "aralkoxyalkyl" refers to the group -alkylenyl-O-aralkyl, where aralkyl is a lower aralkyl.

"Cycloalkyl" refers to a mono- or polycyclic, lower alkyl substituent. Typical cycloalkyl substituents have from 3 to 8 backbone (i.e., ring) atoms in which each backbone atom is optionally substituted carbon. When used in context with cycloalkyl substituents, the term "polycyclic" refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

The term "cycloheteroalkyl" refers herein to cycloalkyl substituents that have from 1 to 5 heteroatoms, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpyrrolidinyl, pyrrolidinonyl, and the like.

The terms "(cycloalkyl)alkyl" and "(cycloheteroalkyl)alkyl" refer to alkyl chains substituted with cycloalkyl and cycloheteroalkyl groups respectively.

The term "haloalkoxy" refers to an alkoxy radical substituted with one or more halogen atoms. The term "halo lower alkoxy" refers to a lower alkoxy radical substituted with one or more halogen atoms.

"Halo" refers herein to a halogen radical, such as fluorine, chlorine, bromine, or iodine.

"Aryl" refers to monocyclic and polycyclic aromatic groups, or fused ring systems having at least one aromatic ring having from 3 to 14 backbone carbon atoms. Examples of aryl groups include without limitation phenyl, naphthyl, dihydronaphtyl, tetrahydronaphthyl, and the like.

"Aralkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

The term "heteroaryl" refers herein to aryl groups having from one to four heteroatoms as ring atoms in an aromatic ring with the remainder of the ring atoms being aromatic or non-aromatic carbon atoms. When used in connection with aryl substituents, the term "polycyclic" refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

"Amino" refers herein to the group —NH$_2$. The term "lower alkylamino" refers herein to the group —NRR' where R and R' are each independently selected from hydrogen or loweralkyl. The term "arylamino" refers herein to the group —NRR' where R is aryl and R' is hydrogen, lower alkyl, aryl, or aralkyl. The term "aralkylamino" refers herein to the group —NRR' where R is aralkyl and R' is hydrogen, lower alkyl, aryl, or aralkyl. The terms "heteroarylamino" and heteroaralkylamino" are defined by analogy to arylamino and aralkylamino.

The term "aminocarbonyl" refers herein to the group —C(O)—NH.sub.2. The terms "lower alkylaminocarbonyl", arylaminocarbonyl", "aralkylaminocarbonyl", "heteroarylaminocarbonyl", and "heteroaralkylaminocarbonyl" refer to —C(O)NRR' where R and R' independently are hydrogen and optionally substituted lower alkyl, aryl, aralkyl, heteroaryl, and heteroaralkyl respectively by analogy to the corresponding terms above.

The term "thio" refers to —SH. The terms "loweralkylthio", "arylthio", "heteroarylthio", "cycloalkylthio", "cycloheteroalkylthio", "aralkylthio", "heteroaralkylthio", "(cycloalkyl)alkylthio", and "(cycloheteroalkyl)alkylthio" refer to —SR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

The term "sulfonyl" refers herein to the group —SO$_2$—. The terms "lower alkylsulfonyl", "arylsulfonyl", "heteroarylsulfonyl", "cycloalkylsulfonyl", "cycloheteroalkylsulfonyl", "aralkylsulfonyl", "heteroaralkylsulfonyl", "(cycloalkyl)alkylsulfonyl", and "(cycloheteroalkyl)alkylsulfonyl" refer to —SO$_2$R where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

The term "sulfinyl" refers herein to the group —SO—. The terms "lower alkylsulfinyl", "arylsulfinyl", "heteroarylsulfinyl", "cycloalkylsulfinyl", "cycloheteroalkylsulfinyl", "aralkylsulfinyl", "heteroaralkylsulfinyl", "(cycloalkyl)alkylsulfinyl", and "(cycloheteroalkyl)alkylsulfinyl" refer to —SOR where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Formyl" refers to —C(O)H.

"Carboxyl" refers to —C(O)OH.

"Carbonyl" refers to the divalent group —C(O)—. The terms "lower alkylcarbonyl", "arylcarbonyl", "heteroarylcarbonyl", "cycloalkylcarbonyl", "cycloheteroalkylcarbonyl", "aralkycarbonyl", "heteroaralkylcarbonyl", "(cycloalkyl)alkylcarbonyl", and "(cycloheteroalkyl)alkylcarbonyl" refer to —C(O)R, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Thiocarbonyl" refers to the group —C(S)—. The terms "lower alkylthiocarbonyl", "arylthiocarbonyl", "heteroarylthiocarbonyl", "cycloalkylthiocarbonyl", "cycloheteroalkylthiocarbonyl", "aralkythiocarbonyloxithiocarbonyl", "heteroaralkylthiocarbonyl", "(cycloalkyl)alkylthiocarbonyl", and "(cycloheteroalkyl)alkylthiocarbonyl" refer to —C(S)R, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonyloxy" refers generally to the group —C(O)—O—. The terms "lower alkylcarbonyloxy", "arylcarbonyloxy", "heteroarylcarbonyloxy", "cycloalkylcarbonyloxy", "cycloheteroalkylcarbonyloxy", "aralkycarbonyloxy", "heteroaralkylcarbonyloxy", "(cycloalkyl)alkylcarbonyloxy", "(cycloheteroalkyl)alkylcarbonyloxy" refer to —C(O)OR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Oxycarbonyl" refers to the group —O—C(O)—. The terms "lower alkyloxycarbonyl", "aryloxycarbonyl", "heteroaryloxycarbonyl", "cycloalkyloxycarbonyl", "cycloheteroalkyloxycarbonyl", "aralkyoxycarbonyloxloxycarbonyl", "heteroaralkyloxycarbonyl", "(cycloalkyl)alkyloxycarbonyl", "(cycloheteroalkyl)alkyloxycarbonyl" refer to —O—C(O)R, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonylamino" refers to the group —NH—C(O)—. The terms "lower alkylcarbonylamino", "arylcarbonylamino", "heteroarylcarbonylamino", "cycloalkylcarbonylamino", "cycloheteroalkylcarbonylamino", "aralkylcarbonylamino", "heteroaralkylcarbonylamino", "(cycloalkyl)alkylcarbonylamino", and "(cycloheteroalkyl)alkylcarbonylamino" refer to —NH—C(O)R, where R is optionally substituted lower alkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes N-substituted carbonylamino (—NR'C(O)R), where R' is optionally substituted lower alkyl, aryl, heteroaryl, aralkyl, or heteroaralkyl and R retains the previous definition.

"Carbonylthio" refers to the group —C(O)—S—. The terms "lower alkylcarbonylthio", "arylcarbonylthio", "heteroarylcarbonylthio", "cycloalkylcarbonylthio", "cycloheteroalkylcarbonylthio", "aralkycarbonylthio", "heteroaralkylcarbonylthio", "(cycloalkyl)alkylcarbonylthio", "(cycloheteroalkyl)alkylcarbonylthio" refer to —C(O)SR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

As used herein, the term "guanidino" or "guanidyl" refers to moieties derived from guanidine, $H_2N—C(.dbd.NH)—NH_2$. Such moieties include those bonded at the nitrogen atom carrying the formal double bond (the "2"-position of the guanidine, e.g., diaminomethyleneamino, $(H_2N)_2C.dbd.NH—$) and those bonded at either of the nitrogen atoms carrying a formal single bond (the "1-" and/or "3"-positions of the guanidine, e.g., $H_2N—C(.dbd.NH)—NH—$). The hydrogen atoms at either nitrogen can be replaced with a suitable substituent, such as loweralkyl, aryl, or loweraralkyl.

As used herein, the term "amidino" refers to the moieties R—C(.dbd.N)—NR'— (the radical being at the "N" nitrogen) and R(NR')C.dbd.N— (the radical being at the "$N_2$" nitrogen), where R and R' can be hydrogen, lower alkyl, aryl, or lower aralkyl.

The term "imino" refers to the group —C(.dbd.NR)—, where R can be hydrogen or optionally substituted lower alkyl, aryl, heteroaryl, or heteroaralkyl respectively. The terms "lower iminoalkyl", "iminocycloalkyl", "iminocycloheteroalkyl", "iminoaralkyl", "iminoheteroaralkyl", "(cycloalkyl)iminoalkyl", "(cycloiminoalkyl)alkyl", "(cycloiminoheteroalkyl)alkyl", and "(cycloheteroalkyl)iminoalkyl" refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

The term "oximino" refers to the group —C(.dbd.NOR)—, where R can be hydrogen ("hydroximino") or optionally substituted lower alkyl, aryl, heteroaryl, or heteroaralkyl respectively. The terms "lower oximinoalkyl", "oximinocycloalkyl", "oximinocycloheteroalkyl", "oximinoaralkyl", "oximinoheteroaralkyl", "(cycloalkyl)oximinoalkyl", "(cyclooximinoalkyl)alkyl", "(cyclooximinoheteroalkyl)alkyl", and (cycloheteroalkyl)oximinoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an oximino group, respectively.

The term "methylene" as used herein refers to an unsubstituted, monosubstituted, or disubstituted carbon atom having a formal $sp^3$ hybridization (i.e., —CRR'—, where R and R' are hydrogen or independent substituents).

The term "methine" as used herein refers to an unsubstituted or carbon atom having a formal $sp^2$ hybridization (i.e., —CR.dbd. or .dbd.CR—, where R is hydrogen a substituent).

"Safe and effective amount" as used herein refers to an amount that effective enough to inhibit cancer cell growth in mammals, and more particularly, in humans without severe side effects.

The term "pharmaceutical carrier" means one or more compatible solid or liquid filler diluents or encapsulating substances which are suitable for administration to mammals.

As used herein, the term "heterocycle" or "heterocyclic system" is intended to mean a stable 5 to 7 membered monocyclic or bicyclic or 7 to 10 membered bicyclic heterocyclic ring which is saturated, partially unsaturated, or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, nitrogen in the heterocycle may optionally be quaternized. In particular embodiments when the total number of S and O atoms in the heterocycle exceeds 1, then these heteroatoms are not adjacent to one another. In specific embodiments the total number of S and O atoms in the heterocycle is not greater than 1. As used herein, the term "aromatic heterocyclic system" is intended to mean a stable 5 to 7 membered monocyclic or bicyclic or 7 to 10 membered bicyclic heterocyclic aromatic ring which consists of carbon atoms and from 1 to 4 heterotams independently selected from the group consisting of N, O and S. In even more specific embodiments, the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. More particular heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The term "heteroaryl" as used herein refers to a 5 membered or 6 membered heterocyclic aromatic group that can optionally carry a fused benzene ring and that can be unsubstituted or substituted.

The terms "linear and cyclic heteroalkyl" are defined in accordance with the term "alkyl" with the suitable replacement of carbon atoms with some other atom such as nitrogen or sulfur which would render a chemically stable species.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, meglumine, lysine, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention may be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; for example, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Embodiments of the present invention provide compounds that have useful agonist and/or antagonist activity with respect to mammalian estrogen receptors in addition to compounds, compositions, and methods useful for treating estrogen receptor-mediated disorders in mammals. More particularly, the compounds of the present invention have been found to possess a surprising degree of activity with respect to the alpha-isoforms of human estrogen receptor in MCF-7 breast cancer cells. Thus, the compounds, compositions, and methods described herein have utility in preventing and/or treating a wide variety of estrogen receptor-mediated disorders including, but not limited to, osteoporosis, breast cancer, uterine cancer, and congestive heart disease.

In one aspect, the present invention provides compounds represented by:

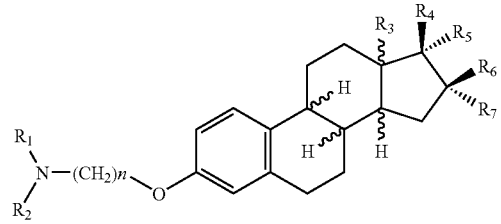

or a stereoisomer, enantiomer, rotomer, tautomer or a pharmaceutically acceptable salt thereof, wherein:

a) $R_1$ and $R_2$ are independently selected from the group consisting of hydrogen, alkyl having 1 to 8 carbon atoms, and nitrogen to form a saturated 5 to 6 ring heterocycle, b) $R_3$ is α or β methyl, c) n is an integer from 2 to 10, d) $R_4$ is selected from the group consisting of hydrogen, hydroxy, ethynyl, fluorine, chlorine, bromine, iodine and acyloxy of a organic carboxylic acid of from 1 to 10 carbon atoms or taken together with the nitrogen to form a saturated 5 to 6 ring heterocycle optionally containing a second nitrogen or oxygen in the ring, carboxylic acid alkyl, alkenyl and alkynyl of from 1 to 10 carbons, f) $R_5$ is selected from the group consisting of hydrogen, hydroxy, ethynyl, fluorine, chlorine, bromine, iodine and acyloxy of a organic carboxylic acid of from 1 to 10 carbon atoms or taken together with the nitrogen to form a saturated 5 to 6 ring heterocycle optionally containing a second nitrogen or oxygen in the ring, carboxylic acid alkyl, alkenyl and alkynyl of from 1 to 10 carbons, and f) $R_6$ and $R_7$ are independently selected from the group consisting of hydrogen, hydroxy, ethynyl, fluorine, chlorine, bromine, iodine and acyloxy of an organic carboxylic acid of from 1 to 10 carbons.

In another aspect, the present invention provides compounds represented by:

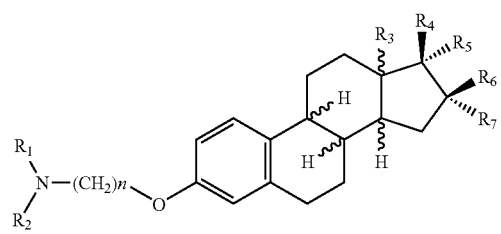

or a stereoisomer, enantiomer, rotomer, tautomer or a pharmaceutically acceptable salt thereof, wherein:

a) $R_1$ and $R_2$ are independently selected from the group consisting of hydrogen, alkyl having 1 to 8 carbon atoms, and nitrogen to form a saturated 5 to 6 ring heterocycle, b) $R_3$ is α or β methyl, c) n is an integer from 2 to 10, d) $R_4$ and $R_5$ form a double-bond with oxygen (=O) or hydroximino (=NOH), and e) $R_6$ and $R_7$ are independently selected from the group consisting of hydrogen, hydroxy, ethynyl, fluorine, chlorine, bromine, iodine and acyloxy of an organic carboxylic acid of from 1 to 10 carbons.

The method of use disclosed is directed to various classes of aminoalkyloxy derivatives of 1,3,5(10)-Estratrien steroids as agents in the treatment of cancer in mammals. The relevant compounds used in the treatment of cancer are represented by:

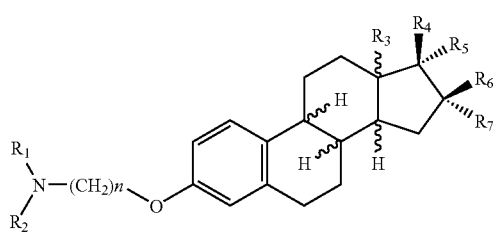

or a stereoisomer, enantiomer, rotomer, tautomer or a pharmaceutically acceptable salt thereof, wherein:

a) $R_1$ and $R_2$ are independently selected from the group consisting of hydrogen, alkyl having 1 to 8 carbon atoms, and nitrogen to form a saturated 5 to 6 ring heterocycle, b) $R_3$ is α or β methyl, c) n is an integer from 2 to 10, d) $R_4$ is selected from the group consisting of hydrogen, hydroxy, ethynyl, fluorine, chlorine, bromine, iodine and acyloxy of an organic carboxylic acid of from 1 to 10 carbon atoms or taken together with the nitrogen to form a saturated 5 to 6 ring heterocycle optionally containing a second nitrogen or oxygen in the ring, carboxylic acid and alkyl, alkenyl and alkynyl of from 1 to 10 carbons, e) $R_5$ selected from the group consisting of hydrogen, hydroxy, ethynyl, fluorine, chlorine, bromine, iodine and acyloxy of an organic carboxylic acid of from 1 to 10 carbons atoms and alkyl, alkenyl and alkynyl of from 1 to 10 carbons, and f) $R_6$ and $R_7$ are independently selected from the group consisting of hydrogen, hydroxy, ethynyl, fluorine, chlorine, bromine, iodine and acyloxy of an organic carboxylic acid of from 1 to 10 carbons.

The relevant compounds used in the treatment of cancer may also be represented by:

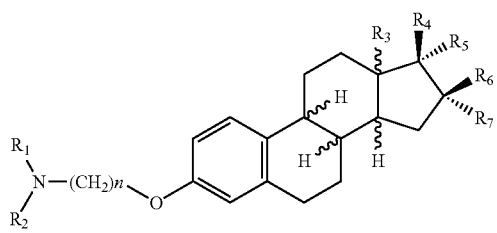

or a stereoisomer, enantiomer, rotomer, tautomer or a pharmaceutically acceptable salt thereof, wherein:

a) $R_1$ and $R_2$ are independently selected from the group consisting of hydrogen, alkyl having 1 to 8 carbon atoms, and nitrogen to form a saturated 5 to 6 ring heterocycle, b) $R_3$ is α or β methyl, c) n is an integer from 2 to 10, d) $R_4$ and $R_5$ form a double-bond with oxygen (=O) or hydroximino (=NOH), and e) $R_6$ and $R_7$ are independently selected from the group consisting of hydrogen, hydroxy, ethynyl, fluorine, chlorine, bromine, iodine and acyloxy of an organic carboxylic acid of from 1 to 10 carbons.

The relevant compounds include, for example one or more of the following:

17β)-3-[2-dimethylamino]-ethoxy]-$\Delta^{1,3,5(10)}$-estrien-17-ol, (17β)-3-[2-diethylamino]-ethoxy]-]-$\Delta^{1,3,5(10)}$-estrien-17-ol, (17β)-3-[2-diisopropylamino]-ethoxy]-]-$\Delta^{1,3,5(10)}$-estrien-17-ol, (17β)-3-[2-morpholinyl]-ethoxy]-]-$\Delta^{1,3,5(10)}$-estrien-17-ol, (17β)-3-[2-piperidinyl]-ethoxy]-]-$\Delta^{1,3,5(10)}$-estrien-17-ol, and (17β)-3-[2-pyrrolidinylamino]-ethoxy]-]-$\Delta^{1,3,5(10)}$-estrien-17-ol.

Pharmaceutical Compositions

The compounds of the present invention can be used in the form of salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepro-pionate, dodecylsulfate, ethanesulfonate, glucoheptanoate, glycerophosphate, hemi-sulfate, heptanoate, hexanoate, fumarate, hydrochloride, hydrodromide, hydroiodide, 2-hydroxyethanesulfonate, lactate, maleate, methanesulfonate, nicotinate, 2-naphth-alenesulfonate, oxalate, pamoate, pectinate, sulfate, 3-phenylpropionate, picrate, pivalate, propionate, succinate, tartrate, p-toluenesulfonate and undecanoate. Also, any basic nitrogen-containing groups can be quaternized with agents such as loweralkyl halides, such as methyl, ethyl, propyl, and butylchloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid, and phosphoric acid, and organic acids such as oxalic acid, maleic acid, succinic acid and citric acid. Basic addition salts can be prepared in situ during the final isolation and purification of the compounds of the invention, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including but not limited to ammonium, tetramethylammonium, tetraethylammonium, methylamine, dimethylamine, trimethylamine, triethylamino, ethylamine, and the like. Other representative organic amines useful for the formation of base addition salts include diethylamine, ethylenediamine, ethanolamine, diethanolamine, piperazine and the like.

In accordance with other embodiments of the present invention, there is provided a composition comprising an estrogen receptor-modulating compound of the present invention, together with a pharmaceutically acceptable carrier or excipient.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-beta-cyclodextrin, polyvinylpyrrolidinone, low melting waxes, ion exchange resins, and the like, as well as combinations of any two or move thereof. Other suitable pharmaceutically acceptable excipients are described in Remington's Pharmaceutical Sciences, Mack Pub. Co., N.J. (1991), incorporated herein by reference in its entirety.

Pharmaceutical compositions containing estrogen receptor modulating compounds of the present invention embodiments may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptably oils or fats, and the like, as well as mixtures of two or more thereof. The liquid carrier may contain other suitably pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, enterally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injection, intravenous, intramuscular, intrasternal injection, intraperitoneal, or infusion techniques.

Injectable preparation includes, for example, sterile injectable aqueous or oleginous suspensions that may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the compound can be prepared by mixing the compound with a suitable nonirritating excipient such as cocoa butter and polyethylene glycols that are solid at ordinary temperatures but liquid at the rectal temperature and will therefore melt in the rectum and release the compound.

Solid dosage forms for oral administration may include capsules, tablets, pills, powders, and granules. In such solid dosage form, the active compound may be admixed with at least one inert diluent such as sucrose lactose or starch. Such dosage forms may also comprise, as is normal practice, additional substances other than inert diluents, for example, lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspension, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. Particular lipids are the phospholipids and phosphatidyl cholines (lecithins), both natural and synthetic. Methods to form liposomes are known in the art (Prescott 1976).

While the compounds of the invention can be administered as the active pharmaceutical agent, they can also be used in combination with one or more other compounds as described herein, and/or in combination with other agents used in the treatment and/or prevention of estrogen receptor-mediated disorders. Alternatively, embodiments of the present invention can be administered sequentially with one or more such agents to provide sustained therapeutic and prophylactic effects. Suitable agents include, but are not limited to, other SERMs as well as traditional estrogen agonists and antagonists. Representative agents useful in combination with the compounds of the invention for the treatment of estrogen receptor-mediated disorders include, for example, tamoxifen, 4-hydroxytamoxifen, raloxifene, toremifene, droloxifene, TAT-59, idoxifene, RU 58,688, EM 139, ICI 164,384, ICI 182,780, clomiphene, MER-25, DES, nafoxidene, CP-336, 156, GW5638, LY139481, LY353581, zuclomiphene, enclomiphene, ethamoxytriphetol, delmadinone acetate, bisphosphonate, and the like. Other agents that can be combined with one or more of the compounds of the invention include aromatase inhibition such as, but not limited to, 4-hydroxyandrostendione, plomestane, exemestane, aminogluethimide, rogletimide, fadrozole (twice), vorozole, letrozole, and anastrozole.

Still other agents useful for combination with the compounds of the invention include, but are not limited to anti-neoplastic agents, such as alkylating agents. Other classes of relevant antineoplastic agents include antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylmelamines such as altretamide, triethylenemelamine, triethylenephosphoramide, triethylenethiophosphoramide and trimethylolmelamine; nitrogen mustards such as chlorambucil, chlornaphazine, cyclophosphamide, estramustine, iphosphamide, mechlorethanine, mechlorethamine oxide hydrochloride, melphtalan, novembichine, phenesterine, prednimustine, trofosfamide, and uracil mustard; nitroso urea, such as carmustine, chlorozotocin, fotemustine, lomustine, nimustine, ranimustine, dacarbazine, mannomustine, mitobronitol, mitolactol, mitolactol and pipobroman.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kasugamycin, kirromycin, and O-methyl threonine, modeccin, neomycin, norvaline, pactanycin, paromomycine, puromycin, ricin, alpha-sarcin, shiga toxin, showdomycin, sparsomycin, spectinomycin, streptomycin, tetracycline, thiostrepton and trimethoprin. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, beta-1-D-arabinoside, amethopterin, aminopterin, 2-aminopurine, aphidiolin, 8-azaguanine, azaserine, 6-azauracil, 2'-azido-2'-deoxynucleosides, 5-bromodeoxycytidine, cytsine, .beta.-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine, and RNA synthesis inhibitors including actinomycin D, alpha-amanitine and other fungal amatoxins, cordycepin (3'-deoxyadenosine), dichloroibofuranosyl benzimidazole, rifampicine, streptovarin and streptolydigin also can be combined with the compounds of the invention to provide pharmaceutical compositions. Other agents will be known to those having skill in the medicinal chemistry and oncology arts.

In addition, the compounds of the present invention, in embodiments, can be used, either singly or in combination as described above, in combination with other modalities for preventing or treating estrogen receptor-medicated disease or disorders. Such other treatment modalities include without limitation, surgery, radiation, hormone supplementation, and diet regulation. These can be performed sequentially such as, for example, treatment with a compound of the invention following surgery or radiation or in combination (e.g., in addition to a diet regimen).

In other embodiments, the present invention includes compounds and compositions in which a compound of the invention is either combined with, or covalently bound to, a cytotoxic agent bound to a targeting agent, such as a monoclonal antibody, for example, a humanized monoclonal antibody. It will be appreciated that the latter combination may allow the introduction of cytotoxic agents into cancer cells with greater specifically. Thus, the active form of the cytotoxic agent (i.e., the free form) will be present only in cells targeted by the antibody. Of course, the compounds of the invention may also be combined with monoclonal antibodies that have therapeutic activity against cancer.

The additional active agents may generally be employed in therapeutic amounts as indicated in the PHYSICIANS' DESK REFERENCE (PDR) 53rd Edition (1999), which is incorporated herein by reference in its entirety, or such therapeutically useful amounts as would be known to one of ordinary skill in the art. The compounds of the invention and the other therapeutically active agents can be administered at the recommended maximum clinical dosage or a lower dosage. Dosage levels of the active compounds in the compositions of the invention may be varied in order to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

In accordance with the yet other embodiments, the present invention provides methods for treating or preventing an estrogen receptor-mediated disorder in a mammalian subject in which an amount of an estrogen receptor-modulating compound modulates estrogen receptor activity in the subject. Other embodiments provide methods for treating a cell or an estrogen receptor-mediated disorder in a mammalian subject, said methods comprising administering to the cell or to the human or mammalian subject an amount of a compound or composition of the invention effective to modulate estrogen receptor activity in the cell or mammalian subject.

Effective amounts of the compound of the invention generally include any amount sufficient to detectably modulate estrogen receptor activity by any of the assays described herein, by other activity assays known to those having ordinary skill in the art, or by the detection, prevention or alleviation of symptoms in a subject afflicted with an estrogen receptor-mediated disorder.

Estrogen receptor-mediated disorders that may be treated in accordance with the invention include any biological or medical disorder in which estrogen receptor activity is implicated or in which the inhibition of estrogen receptor potentiates or retards signaling through a pathway that is characteristically defective in the disease to be treated. The condition or disorder may either be caused or characterized by abnormal estrogen receptor activity. Representative estrogen receptor-mediated disorders include, for example, osteoporosis, atherosclerosis, estrogen-mediated cancers (e.g., breast and endometrial cancer). Other disorders include Turner's syndrome, benign prostate hyperplasia (i.e., prostate enlargement), prostate cancer, elevated cholesterol, restenosis, endometriosis, uterine fribroid disease, skin and/or vagina atrophy, and Alzheimer's disease. Successful treatment of a subject in accordance with the invention may result in the prevention, inducement of a reduction in, or alleviation of symptoms in a subject afflicted with an estrogen receptor-mediated medical or biological disorder. Thus, for example, treatment can result in a reduction in breast or endometrial tumors and/or various clinical markers associated with such cancers. Likewise, treatment of Alzheimer's disease can result in a reduction in the rate of disease progression, detected, for example, by measuring a reduction in the rate of increase of dementia.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age of the patient, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg/kg/day to about 100 mg/kg/day, more specifically from about 1 mg/kg/day to about 20 mg/kg/day, and most specifically from about 2 mg/kg/day to about 10 mg/kg/day of a estrogen receptor-modulating compound of the present invention, which may be administered in one or multiple doses.

EXAMPLES

The following Examples are provided to illustrate certain aspects of the present invention and to aid those of skill in the art in practicing the invention. These Examples are in no way to be considered to limit the scope of the invention in any manner.

Preparation of Compounds of the Invention

The following procedure was used in embodiments to synthesize the compounds. Sodium metal (3 mole equivalent) was dissolved in about 50 mL of ethanol. To this solution a 1 mole equivalent of the steroid was added. To the resulting solution alkylamine chloride, 1.2 mole equivalent was added and refluxed for about 17 hours. The mixture was then filtered and the filtrate was concentrated to dryness. The residue was re-dissolved in 150 mL of ethyl acetate and washed with 0.1 N aqueous hydrochloric acid (2×100 mL), then 2 N sodium hydroxide (2×100 mL) and water (100 mL). The organic layer was dried over magnesium sulfate, filtered and concentrated under reduced pressure to obtain the residue. The residue was dissolved in 100 mL of diethyl ether and acidified with gaseous hydrochloric acid to reach a pH of about 3. The acidified mixture was filtered, washed with ether and solid collected. Impurities in the solid were removed and analyzed by preparative TLC or by flash chromatography. The following is an illustrative list of the compounds, but is not meant to be an exhaustive list of the compounds falling within the broad scope of this disclosure.

The hydrochloric salts of the compounds were prepared using methanolic hydrochloric solution. Trans-4-Hydroxytamoxifen was purchased from Sigma-Aldrich company and its HCl salt was prepared using methanolic HCl solution to avoid isomerization which occurs with the basic free amine species. The HCl salts of the compounds of structures I-III were compared with trans-4-hydroxytamoxifen in groups of four. However, preparation of the compounds was not necessarily limited to salt forms, but may include free base forms.

General Procedures

All reagents obtained from commercial sources were used without further purification. Anhydrous solvents were obtained from commercial sources and used without further drying. Separation and purification of the products were carried out using any single or combination of the following methods. Flash column chromatography was performed with silica gel, 200-400 mesh, 60 A obtained from Fisher Scientific, St. Louis, Mo. Typical solvents employed were dichloromethane (DCM), methanol (MeOH), ethyl acetate (EtOAc), and hexanes (Hex). Preparative TLC was conducted using 20 times 20 cm plates coated with silica gel.

Steroids were purchased from Steroloids Inc. (Newport, R.I.). $^1$H NMR spectra were obtained with a spectrometer and chemical shifts are reported in parts per million (ppm) using tetramethylsilane as an internal reference.

Thus, the present invention will be seen to provide new compounds that have strong estrogen receptor-modulating action. These compounds can be employed in compositions and methods for treating estrogen receptor-mediated disorders, such as osteoporosis, breast and endometrial cancer, Alzheimer's disease, and atherosclerosis.

The disclosure above is for the purposes of illustration and not limitation. Those having skill in the arts relevant to the present invention will appreciate from the foregoing the present invention encompasses many additional embodiments of the invention that are not described explicitly, but which nevertheless are provided by the teachings of the present invention. Such additional embodiments include, but are not limited to, estrogen receptor-mediated diseases other than osteoporosis, breast and endometrical cancer, alzheimers's disease, and atherosclerosis, that are preventable or treatable using the compounds, compositions, and methods of the invention. Still other aspects include compounds that can be designed, synthesized, and tested for therapeutic or prophylactic effect using the teachings of the foregoing disclosure.

Abbreviations which are used in the Examples 1-18 that follow are:

Δ: An indication of location of double bond in structure at 1,3,5(10)

δ: An indication of peaks in the NMR spectrum

DMSO: Dimethyl sulfoxide

MHZ: mega hertz d6: Deuteriated solvent

NMR: nuclear magnetic resonance

S: singlet peak br: broad m: multiplet peaks d: doublet peak $^1$H: proton

2H: The number of protons associated with the peak

α: An indication that the functional group is below the plane of the structure

β: An indication that the functional group is above the plane of the structure

J: The coupling constant, the distance between peaks in a multiplet.

Example 1

3-[2-diethylamino]-ethoxy]-]-Δ$^{1,3,5(10)}$-estrien-17α-ethynyl-17β-ol

Using the general procedure, the product was obtained in 28% yield as a solid.

$^1$H-NMR (500 MHz, d$_6$-DMSO) δ 0.74 (s, 3H), 1.24 (m, 18H), 1.72 (m, 7H), 2.0 (m, 3H) 2.76 (br s, 2H), 6.69 (m, 2H) 7.2 (d, 1H, J=6 Hz), 7.68 (s, 1H), 10.09 (br s, 1H).

Example 2

3-[2-morpholinyl]-ethoxy]-]-Δ$^{1,3,5(10)}$-estrien-17α-ethynyl-17β-ol

Using the procedure described above, the product was obtained in 64% yield as a solid.

$^1$H-NMR (500 MHz, d$_6$-DMSO) δ 0.74 (s, 3H), 1.3 (m, 4H), 1.7 (m, 7H) 2.0 (m, 2H), 2.3 (d, 1H, J=12 Hz), 2.76 (br s, 2H), 3.42 (m, 4H), 3.87 (m, 4H), 4.37 (br s, 2H), 5.34 (br s, 1H), m 6.68 (m, 2H), 7.19 (d, 2H, J=6 Hz), 11.55 (br s, 1H)

Example 3

3-[2-dimethylamino]-ethoxy]-]-Δ$^{1,3,5(10)}$-estrien-17α-ethynyl-17β-ol

Using the procedure described above, the product was obtained in 25% yield as a solid.

$^1$H-NMR (500 MHz, d$_6$-DMSO) δ 0.74 (s, 3H), 1.27 (m, 10H), 1.7 (m, 8H), 2.08 (m, 2H) 2.32 (m, 1H), 4.2 (m, 3H), 6.69 (m, 3H), 7.19 (d, 1H J=9 Hz), 7.68 (s 1H), 10.48 (br s, 1H)

Example 4

3-[2-pyrrolidinylamino]-ethoxy]-]-Δ$^{1,3,5(10)}$-estrien-17α-ethynyl-17βol

Using the procedure described above, the product was obtained in 35% yield as a solid.

$^1$H-NMR (500 MHz, d$_6$-DMSO) δ 0.74 (s, 3H), 1.3 (m, 5H), 2.1-1.88 (m, 14 H) 2.31 (m, 1H), 2.77 (br s, 3H), 3.07 (br s, 3H) 4.26 (br s, 2H) 5.33 (br s 1H) 6.72 (m, 2H), 7.19 (d, 1H J=9 Hz), 10.54 (br s, 1H)

Example 5

3-[2-piperidinyl]-ethoxy]-]-Δ$^{1,3,5(10)}$-estrien-17α-ethynyl-17β-ol

Using the procedure described above, the product was obtained in 60% yield as a solid.

$^1$H-NMR (500 MHz, d$_6$-DMSO) δ 0.74 (s, 3H), 1.34 (m, 6H), 1.7 (m, 12H), 2.08 (m, 2H), 2.31 (m, 1H), 2.76 (br s, 1H), 2.97 (m, 2H), 3.44 (m, 4H), 4.30 (br s, 1H), 5.35 (br s, 1H) 6.68 (m, 2H), 7.19 (d, 1H J=9 Hz), 9.94 (br s, 1H)

Example 6

3-[2-diisopropylamino]-ethoxy]-]-Δ$^{1,3,5(10)}$-estrien-17α-ethynyl-17β-ol

Using the procedure described above, the product was obtained in 43% yield as a solid.

$^1$H-NMR (500 MHz, d$_6$-DMSO) δ 0.68 (s, 3H), 1.13 (t, 2H J=24 Hz), 1.28 (m, 12H), 1.6 (m, 5H), 1.8 (m, 5H), 2.07 (m, 2H), 3.48 (m, 3H), 2.30 (m, 2H), 2.77 (br s, 2H), 3.22 (m, 2H) 6.68 (m, 2H), 7.20 (d, 1H J=6 Hz), 9.80 (br s, 1H)

Example 7

3-[2-diethylamino]-ethoxy]-]-Δ$^{1,3,5(10)}$-estrien-17-one

Using the procedure described above, the product was obtained in 53% yield as a solid.

$^1$H-NMR (300 MHz, d$_6$-DMSO) δ 0.81 (s, 3H), 1.35 (m, 10H), 2.1 (m, 8H), 2.08 (m, 3H) 2.32 (m, 1H), 2.81 (br s, 3H) 3.4 (br s, 3H), 6.70 (m, 2H), 7.19 (d, 1H J=9 Hz), 10.70 (br s, 1H)

Example 8

3-[2-dimethylamino]-ethoxy]-]-Δ$^{1,3,5(10)}$-estrien-17-one

Using the procedure described above, the product was obtained in 42% yield as a solid.

$^1$H-NMR (300 MHz, d$_6$-DMSO) δ 0.81 (s, 3H), 1.37 (m, 8H), 1.7 (m, 8H), 2.2 (m, 2H) 2.79 (br s, 6H), 6.73 (m, 2H), 7.19 (d, 1H J=9 Hz), 7.68 (s 1H), 10.72 (br s, 1H)

Example 9

3-[2-pyrrolidinylamino]-ethoxy]-]-Δ$^{1,3,5(10)}$-estrien-17-one

Using the procedure described above, the product was obtained in 60% yield as a solid.

$^1$H-NMR (300 MHz, d$_6$-DMSO) δ 0.81 (s, 3H), 1.49 (m, 7H), 1.7 (m, 8H), 2.81 (m, 2H) 3.06 (m, 2H), 3.5 (br s, 3H) 4.2 (m, 2H), 6.69 (m, 2H), 7.19 (d, 1H J=6 Hz), 7.68 (s 1H), 11.07 (br s, 1H)

Example 10

3-[2-piperidinyl]-ethoxy]-]-Δ$^{1,3,5(10)}$-estrien-17-one

Using the procedure described above, the product was obtained in 69% yield as a solid.

$^1$H-NMR (300 MHz, d$_6$-DMSO) δ 0.81 (s, 3H), 1.35 (m, 12H), 2.09 (m, 2H), 2.4 (m, 2H), 2.9 (m, 5H), 3.4 (m, 4H), 4.3 (m, 3H), 6.7 (m, 2H), 7.19 (d, 1H J=9 Hz), 10.89 (br s, 1H)

Example 11

3-[2-diisopropylamino]-ethoxy]-]-Δ$^{1,3,5(10)}$-estrien-17-one

Using the procedure described above, the product was obtained in 44% yield as a solid.

$^1$H-NMR (300 MHz, d$_6$-DMSO) δ 0.81 (s, 3H), 1.24 (m, 14H), 1.3 (m, 12H), 1.8 (m, 2H), 2.12 (m, 2H), 4.2 (m, 2H) 6.67 (m, 2H) 7.2 (d, 1H, J=9 Hz), 7.68 (s, 1H), 9.55 (br s, 1H)

Example 12

3-[2-morpholinyl]-ethoxy]-]-Δ$^{1,3,5(10)}$-estrien-17-one

Using the procedure described above, the product was obtained in 65% yield as a solid.

¹H-NMR (300 MHz, d₆-DMSO) δ 0.81 (s, 3H), 1.3 (m, 10H), 2.81 (m, 4H), 3.4 (m, 4H), 3.8 (m, 6H), 4.24 (t, 2H J=9 Hz), 4.37 (br s, 2H), 6.69 (m, 2H) 7.2 (d, 1H, J=9 Hz), 11.39 (br s, 1H)

Example 13

(17β)-3-[2-diethylamino]-ethoxy]-]-Δ$^{1,3,5(10)}$-estrien-17-ol

Using the procedure described above, the product was obtained in 83% yield as a solid.

1H-NMR (300 MHz, d₆-DMSO) δ 0.65 (s, 3H), 1.3 (m, 10H), 1.82 (m, 3H), 2.08 (m, 2H), 2.24 (m, 2H), 2.76 (br s, 2H), 3.6 (m, 7H), 4.29 (br s, 3H), 6.63 (m, 2H) 7.2 (d, 1H, J=4 Hz), 7.68 (s, 1H), 9.90 (br s, 1H)

Example 14

(17β)-3-[2-dimethylamino]-ethoxy]-Δ$^{1,3,5(10)}$-estrien-17-ol

Using the procedure described above, the product was obtained in 74% yield as a solid.

1H-NMR (300 MHz, d₆-DMSO) δ 0.65 (s, 3H), 1.28 (m, 8H), 1.25 (m, 3H), 1.8 (m, 5H), 2.08 (m, 2H), 2.25 (m, 2H), 2.79 (br s, 6H) 3.26 (m, 4H) 6.68 (m, 2H) 7.19 (d, 1H, J=6 Hz), 7.68 (s, 1H), 10.54 (br s, 1H)

Example 15

(17β)-3-[2-pyrrolidinylamino]-ethoxy]-]-Δ$^{1,3,5(10)}$-estrien-17-ol

Using the procedure described above, the product was obtained in 66% yield as a solid.

1H-NMR (300 MHz, d₆-DMSO) δ 0.65 (s, 3H), 1.27 (m, 7H), 1.72 (m, 8H), 3.26 (m, 2H) 3.41 (m, 6H), 4.2 (m, 4H) 5.34 (br s, 1H), 6.7 (m, 2H) 7.2 (br s, 1H), 7.68 (s, 1H), 10.81 (br s, 1H)

Example 16

(17β)-3-[2-piperidinyl]-ethoxy]-]-Δ$^{1,3,5(10)}$-estrien-17-ol

Using the procedure described above, the product was obtained in 39% yield as a solid.

1H-NMR (300 MHz, d₆-DMSO) δ 0.81 (s, 3H), 0.85 (br s, 3H), 1.35 (m, 10H), 1.9 (m, 8H), 2.12 (m, 2H), 2.4 (m, 2H), 4.25 (m, 4H), 5.35 (br s, 1H) 6.7 (m, 2H), 7.19 (d, 1H J=9 Hz), 7.68 (s, 1H), 10.89 (br s, 1H)

Example 17

(17β)-3-[2-diisopropylamino]-ethoxy]-]-Δ$^{1,3,5(10)}$-estrien-17-ol

Using the procedure described above, the product was obtained in 73% yield as a solid.

1H-NMR (300 MHz, d₆-DMSO) δ 0.60 (s, 3H), 1.22 (m, 14H), 1.7-2.3 (m, 10H), 2.79 (br s, 2H), 3.15 (br s, 4H), 4.3 (m, 3H) 6.69 (m, 2H), 7.2 (d, 1H J=9 Hz), 7.68 (s, 1H), 10.38 (br s, 1H)

Example 18

(17β)-3-[2-morpholinyl]-ethoxy]-]-Δ$^{1,3,5(10)}$-estrien-17-ol

Using the procedure described above, the product was obtained in 63% yield as a solid.

1H-NMR (300 MHz, d₆-DMSO) δ 0.64 (s, 3H), 1.2 (m, 4H), 1.8 (m, 3H), 2.12 (m, 2H), 2.24 (m, 2H) 2.09 (m, 3H), 2.75 (br s, 3H) 3.15 (m, 3H), 3.47 (m, 5H), 3.88 (m, 4H), 6.68 (m, 2H), 7.18 (d, 1H J=9 Hz), 7.68 (s, 1H), 11.55 (br s, 1H).

The above compounds that were made and analyzed are included in the following structures. The compounds may be used to treat cancer in mammals by administering a safe and effective amount of a pharmaceutical composition comprising compounds selected for the group consisting of compounds according to Structures II-IV.

Structure II

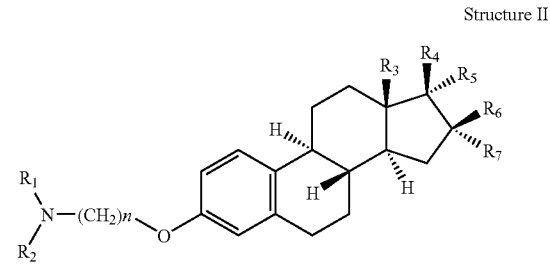

Wherein:

$R_1$ and $R_2$ are independently alkyl of 1 to 8 carbon atoms, taken together with the nitrogen form a saturated 5 to 6 ring heterocycle, n is an integer of from 2 to 10, $R_3$ is β methyl, $R_4$ is hydroxy or hydrogen, $R_5$ is hydrogen or hydroxy, $R_6$ and $R_7$ are hydrogen, and including their pharmaceutically acceptable acid salts.

Structure III

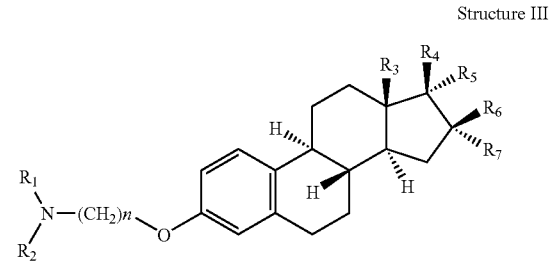

Wherein:

$R_1$ and $R_2$ are independently alkyl having from 1 to 8 carbon atoms, taken together with nitrogen form a saturated 5 to 6 ring heterocycle, n is an integer of from 2 to 10, $R_3$ is β methyl, $R_4$ is hydroxy or ethynyl, $R_5$ is ethynyl or ethynyl, $R_6$ and $R_7$ are hydrogen, and including their pharmaceutically acceptable acid salts.

Structure IV

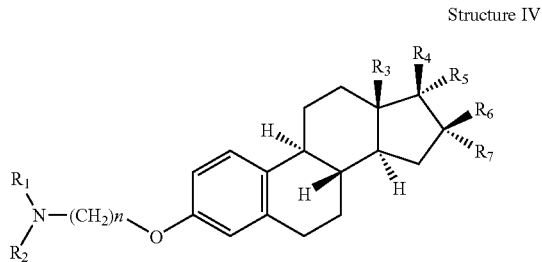

Wherein:

$R_1$ and $R_2$ are independently alkyl having from 1 to 8 carbon atoms taken together with nitrogen form a saturated 5 to 6 ring heterocycle, n is an integer of from 2 to 10, $R_3$ is β methyl, $R_4$ and $R_5$ form a double-bond with oxygen (=O) or hydroximino (=NOH), $R_6$ and $R_7$ are hydrogen, and including their pharmaceutically acceptable salts.

The compounds selected are those having attached groups wherein $R_1$ and $R_2$ are independently alkyl of 1 to 8 carbon atoms or taken together with the nitrogen form a saturated 5 to 6 ring heterocycle. Optionally, if a ring is formed, $R_1$ and $R_2$ may contain a second nitrogen or oxygen in the ring, $R_3$ is alpha or beta-methyl, n is an integer from 2 to 10, $R_4$ and $R_5$ together are double bonded to oxygen (=O) or hydroximino (=NOH) or $R_4$ is independently hydrogen, hydroxyl (—OH), ethynyl, fluorine, chlorine, bromine, iodine and acyloxy of an organic carboxylic acid of up to 12 carbon atoms, and alkyl, alkenyl and alkynyl of up to 8 carbon atoms, and $R_5$ is independently hydrogen, hydroxyl (—OH), ethynyl, fluorine, chlorine, bromine, iodine and acyloxy of an organic carboxylic acid of up to 12 carbon atoms and alkyl, alkenyl and alkynyl of up to 8 carbon atoms, $R_6$ and $R_7$ are double-bonded oxygen or are independently hydrogen, hydroxyl (—OH), ethynyl, fluorine, bromine, chlorine, iodine and acyloxy of an organic carboxylic acid of up to 12 carbon atoms or $R_5$ and $R_6$ form a double bond and $R_4$ and $R_7$ are hydrogen and their non-toxic, pharmaceutically acceptable acid addition salts in an amount sufficient for the treatment of a mammalian cancer.

Examples of $R_1$, $R_2$ and $R_5$ as alkyl of from 1 to 8 carbon atoms consist of methyl, ethyl, propyl, isopropyl, butyl, isobutyl, tert-butyl, n-pentyl, n-hexyl, 2-methylpentyl, 2,3-dimethylbutyl, n-heptyl, 2-methylhexyl, 2,2,-dimethyl-pentyl, 3,3-dimethyl-pentyl, 3-ethylpentyl, n-octyl, 2,2-dimethylhexyl, 3,3-dimethylhexyl and 3-methyl-3-ethylpentyl. Of particular interest are methyl, ethyl, and isopropyl.

In another embodiment $R_1$ and $R_2$ form a heterocyclic ring with nitrogen comprising 5 to 6 members of a heteroatom chosen from oxygen and nitrogen, optionally. In particular piperidinyl, piperazinyl, morpholinyl or pyrrolindinyl ring systems are encompassed in embodiments of this invention.

Examples of acyloxyl of an organic carboxylic acid of up to 12 carbon atoms include, for example, formyloxyl, acetyloxy, propionyloxyl, butyryloxyl, hexanoyloxyl and benzoyloxyl.

Examples of alkenyl having at most 8 carbons are vinyl, allyl, 1-propenyl, butenyl, pentenyl or hexenyl.

Examples of alkynyl having at most 8 carbon atoms are ethynyl, propargyl, butynyl, pentynyl or hexynyl.

Examples of suitable acids for the non-toxic, pharmaceutically acceptable acid salts are hydrochloric acid, hydrobromic acid, nitric acid, sulfuric acid, phosphoric acid, acetic acid, formic acid, propionic acid, benzoic acid, maleic acid, furmaric acid, succinic acid, tartaric acid, citric acid, oxalic acid, glyoxylic acid, aspartic acid, alkane sulfonic acids such as methane or ethane sulfonic acid, arylsulfonic acids such as benzene acid or p-toluene sulfonic acids such as p-toluene sulfonic or benzene acid and arylcarboxylic acids. In particular hydrochloric acid may be used The following structures depict embodiments of compounds for treating cancer in mammals by administering a safe and effective amount of one or more compounds comprised of compounds according to Structure II.

Structure II

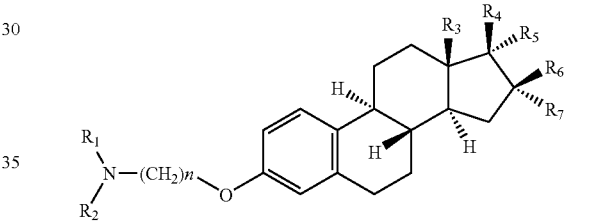

Wherein:

$R_1$ and $R_2$ are independently alkyl of 1 to 8 carbon atoms, taken together with nitrogen form a saturated 5 to 6 ring heterocycle, n is an integer of from 2 to 10, $R_3$ is β methyl, $R_4$ is hydroxy or hydrogen, $R_5$ is hydrogen or hydroxy, $R_6$ and $R_7$ are hydrogen, and including their pharmaceutically acceptable acid salts.

The following compounds found in embodiments of the present invention include, but are not limited to:

17β)-3-[2-dimethylamino]-ethoxy]-$\Delta^{1,3,5(10)}$-estrien-17-ol (17β)-3-[2-diethylamino]-ethoxy]-]-$\Delta^{1,3,5(10)}$-estrien-17-ol (17β)-3-[2-diisopropylamino]-ethoxy]-]-$\Delta^{1,3,5(10)}$-estrien-17-ol (17β)-3-[2-morpholinyl]-ethoxy]-]-$\Delta^{1,3,5(10)}$-estrien-17-ol (17β)-3-[2-piperidinyl]-ethoxy]-]-$\Delta^{1,3,5(10)}$-estrien-17-ol (17β)-3-[2-pyrrolidinylamino]-ethoxy]-]-$\Delta^{1,3,5(10)}$-estrien-17-ol according to the following structure, and

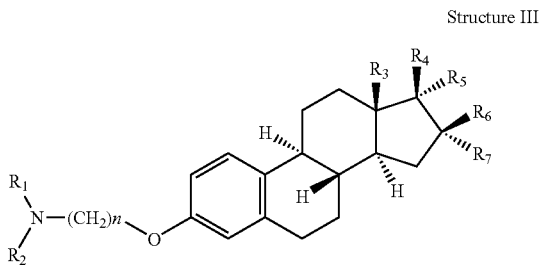

Structure III

Wherein:

$R_1$ and $R_2$ are independently selected from the group consisting of alkyl having from 1 to 8 carbon atoms and when taken together with the nitrogen form a saturated 5 to 6 ring heterocycle, n is an integer of from 2 to 10, $R_3$ is β methyl, $R_4$ is hydroxy or ethynyl, $R_5$ is ethynyl or hydroxy, $R_6$ and $R_7$ are hydrogen, including their pharmaceutically acceptable acid salts. The following compounds included in the scope of this invention include, but are not limited to:

3-[2-dimethylamino]-ethoxy]-]-$\Delta^{1,3,5(10)}$-estrien-17α-ethynyl-17β-ol

3-[2-diethylamino]-ethoxy]-]-$\Delta^{1,3,5(10)}$-estrien-17α-ethynyl-17β-ol

3-[2-diisopropylamino]-ethoxy]-]-$\Delta^{1,3,5(10)}$-estrien-17α-ethynyl-17β-ol 3-[2-morpholinyl]-ethoxy]-]-$\Delta^{1,3,5(10)}$-estrien-17α-ethynyl-17β-ol 3-[2-piperidinyl]-ethoxy]-]-$\Delta^{1,3,5(10)}$-estrien-17α-ethynyl-17β-ol 3-[2-pyrrolidinylamino]-ethoxy]-]-$\Delta^{1,3,5(10)}$-estrien-17α-ethynyl-17βol according to the following structure.

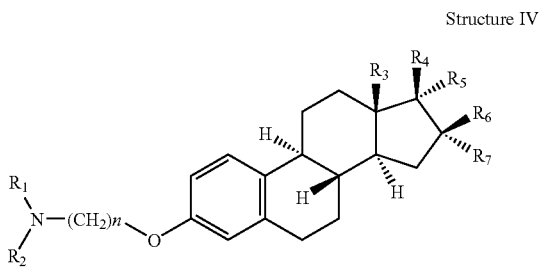

Structure IV

Wherein:

$R_1$ and $R_2$ are independently selected from the group consisting of alkyl having from 1 to 8 carbon atoms and when taken together with nitrogen form a saturated 5 to 6 ring heterocycle, n is an integer of from 2 to 10, $R_3$ is β methyl, $R_4$ and $R_5$ form a double-bond with oxygen (=O) or hydroximino (=NOH), and $R_6$ and $R_7$ are hydrogen.

The following compounds included in embodiments of this invention include, but are not limited to:

3-[2-dimethylamino]-ethoxy]-]-$\Delta^{1,3,5(10)}$-estrien-17-one

3-[2-diethylamino]-ethoxy]-]-$\Delta^{1,3,5(10)}$-estrien-17-one

3-[2-diisopropylamino]-ethoxy]-]-$\Delta^{1,3,5(10)}$-estrien-17-one

3-[2-morpholinyl]-ethoxy]-]-$\Delta^{1,3,5(10)}$-estrien-17-one

3-[2-piperidinyl]-ethoxy]-]-$\Delta^{1,3,5(10)}$-estrien-17-one

3-[2-pyrrolidinylamino]-ethoxy]-]-$\Delta^{1,3,5(10)}$-estrien-17-one

The wavy lines in positions 8, 9 and 14 indicate hydrogen in position 8β, 9α, 14α, or 8α 9β, 14β.

The wavy lines in position 17 indicate that the $R_4$ and $R_5$ groups are in the α or β positions. $R_4$ is in the α position and $R_5$ is in β position or $R_4$ is β position or $R_5$ is in α position.

Among the specific compounds of this invention are those wherein $R_3$ is alpha or beta-methyl, those of the formula wherein $R_1$, $R_2$, $R_5$ and n are defined as above, those of the formula wherein $R_1$ and $R_2$ are independently alkyl of from 1 to 8 carbons atoms, n is defined as above and either $R_4$ is hydrogen or hydroxy and $R_5$ is hydroxy (—OH) or hydrogen or $R_4$ and $R_5$ are both hydrogen or $R_4$ and $R_5$ are double bonded oxygen (=O) or hydroximino (=NOH), those of the formula wherein $R_1$, $R_2$ and n are defined as above and either $R_4$ and $R_5$ are independently hydrogen, hydroxyl (—OH), ethynyl fluorine, chlorine, bromine, iodine and acyloxyl of an organic carboxylic acid of up to 12 carbon atoms and $R_6$ and $R_7$ together form a double bond or are selected from the group consisting of hydrogen, hydroxyl (—OH), ethynyl, fluorine, chlorine, bromine, iodine and acyloxyl of an organic carboxylic acid of up to 12 carbon atoms or $R_5$ and $R_6$ together to form a double bond and $R_4$ and $R_7$ are hydrogen and their nontoxic. More specific compounds of formula 1 are those wherein $R_1$ and $R_2$ are both methyl, ethyl and isopropyl and those wherein n equals 2 or 3, and including and their nontoxic, pharmaceutically acceptable acid salts. In embodiments, the compounds of this disclosure are not limited to the salt forms, but may include free base forms also.

The compounds of Structures I-IV have been shown to exhibit anti-breast cancer activities in assays involving MCF-7 cells. MCF-7 breast cancer cells are estrogen receptor alpha enriched breast cells taken from patients. These compounds shown potent inhibition of the growth of MCF-7 breast cancer cells. These compounds can therefore be used in the treatment of breast cancer in mammals and may also find usefulness in the treatment of endometrial cancer as well.

The compounds can be administered, for example, in the manner suitable for medicinal or pharmacology purposes. The particular route of administration will depend on the kind of cancer and the dosage form chosen. In embodiments, the compounds of Structures I-IV can be administered orally, rectally, vaginally, parenterally or by local route such as subcutaneous in the breast of mammals. Orally, all of the compounds can be in the form of tablets, capsules, granules, suppositories, injectable preparations and vaginal preparations.

Pharmacological Tests

Pharmacological Test

MCF-7 (ATCC HTB-22) cells, purchased from ATCC (Rockville, Md.), were grown in RPMI medium 1640 with 10% FBS (GIBCO, Grand Island, N.Y.) and 1% Antibiotic-Antimycotic (GIBCO, Grand Island, N.Y.) in an incubator (NUAIRE NU-1500, Plymouth, Minn.) with 5% $CO_2$ and 95% air at about 37° Celsius. Cells were grown as monolayer, doubling time is from about 19 to about 24 hours. The stock solution of the test compound was prepared at 1 mg/ml drug concentration. The stock solution was diluted serially to obtain the desired drug concentrations, of from about 20 to about 200 μg/ml. Plates with twelve wells (5 ml capacity/well) were employed for all the experiments. In a typical experiment, each well contained $1\times10^5$ initial cells and about 100 μl drug solution in a total volume of about 2 ml media. The final concentrations of compounds were from about 0 to about 100 μg/ml in triplicate sample wells. The plates were incubated at 5% CO2 and 37° C. for about 72 hours. After incubation, cells were washed with PBS 1×, treated by 0.5 ml trypsin-EDTA for about 10 minutes and the cells were suspended by adding about 1.5 ml medium. Cells were counted by using a hemacytometer under a microscope. The data was converted to micromolar concentration using the various molecular weights and represent the mean values and standard errors.

Tables 1-4 illustrate the $IC_{50}$ (50% inhibitory concentration) values of compounds described in this application against the MCF-7 breast cancer cell line.

TABLE 1

| Structure II Compounds | $IC_{50}$ (micromolar scale) MCF-7 breast cancer cell line |
| --- | --- |
| (17β)-3-[2-dimethylamino]-ethoxy]-$\Delta^{1,3,5(10)}$-estrien-17-ol HCl salt | 16.2 |
| (17β)-3-[2-diethylamino]-ethoxy]-]-$\Delta^{1,3,5(10)}$-estrien-17-ol HCl salt | 8.7 |
| (17β)-3-[2-diisopropylamino]-ethoxy]-]-$\Delta^{1,3,5(10)}$-estrien-17-ol HCl salt | 5.6 |
| (17β)-3-[2-morpholinyl]-ethoxy]-]-$\Delta^{1,3,5(10)}$-estrien-17-ol HCl salt | 19.8 |
| (17β)-3-[2-piperidinyl]-ethoxy]-]-$\Delta^{1,3,5(10)}$-estrien-17-ol HCl salt | 4.1 |
| (17β)-3-[2-pyrrolidinylamino]-ethoxy]-]-$\Delta^{1,3,5(10)}$-estrien-17-ol HCl salt | 10.8 |
| 4-Hydroxytamoxifen HCl salt | 9.0 |

TABLE 2

| Structure III Compounds | $IC_{50}$ (micromolar scale) MCF-7 breast cancer cell line |
| --- | --- |
| 3-[2-dimethylamino]-ethoxy]-]-$\Delta^{1,3,5(10)}$-estrien-17α-ethynyl-17β-ol HCl salt | 9.1 |
| 3-[2-diethylamino]-ethoxy]-]-$\Delta^{1,3,5(10)}$-estrien-17α-ethynyl-17β-ol HCl salt | 7.3 |
| 3-[2-diisopropylamino]-ethoxy]-]-$\Delta^{1,3,5(10)}$-estrien-17α-ethynyl-17β-ol HCl salt | 8.3 |
| 3-[2-morpholinyl]-ethoxy]-]-$\Delta^{1,3,5(10)}$-estrien-17α-ethynyl-17β-ol HCl salt | 21.5 |
| 3-[2-piperidinyl]-ethoxy]-]-$\Delta^{1,3,5(10)}$-estrien-17α-ethynyl-17β-ol HCl salt | 6.1 |
| 3-[2-pyrrolidinylamino]-ethoxy]-]-$\Delta^{1,3,5(10)}$-estrien-17α-ethynyl-17βol HCl salt | 6.4 |
| 4-Hydroxytamoxifen HCl salt | 9.5 |

TABLE 3

| Structure IV Compounds | $IC_{50}$ (micromolar scale) MCF-7 breast cancer cell line |
| --- | --- |
| 3-[2-dimethylamino]-ethoxy]-]-$\Delta^{1,3,5(10)}$-estrien-17-one HCl salt | 37.8 |
| 3-[2-diethylamino]-ethoxy]-]-$\Delta^{1,3,5(10)}$-estrien-17-one HCl salt | 7.5 |
| 3-[2-diisopropylamino]-ethoxy]-]-$\Delta^{1,3,5(10)}$-estrien-17-one HCl salt | 9.2 |
| 3-[2-morpholinyl]-ethoxy]-]-$\Delta^{1,3,5(10)}$-estrien-17-one HCl salt | 20.8 |
| 3-[2-piperidinyl]-ethoxy]-]-$\Delta^{1,3,5(10)}$-estrien-17-one HCl salt | 5.1 |
| 3-[2-pyrrolidinylamino]-ethoxy]-]-$\Delta^{1,3,5(10)}$-estrien-17-one HCl salt | 10.6 |
| 4-Hydroxytamoxifen HCl salt | 10.6 |

The compounds used in embodiments of the present invention can be formulated into pharmaceutical compositions for use in the treatment of cancer cells. Standard pharmaceutical formulation techniques should be used as illustrated in acceptable pharmaceutical texts. A safe and effective amount is an amount that effective enough to inhibit cancer cell growth in warm-blooded mammals, particularly in humans without severe side effects. The "safe and effective amount" of the compound effective to inhibit cancer cell growth may vary depending on the type of cancer cells, the stage of the disease, the physical and biological characteristics of the patient and the duration of the treatment.

The compositions of the subject invention contain at least one pharmaceutical carrier. The term "pharmaceutical carrier" means one or more compatible solid or liquid filler diluents or encapsulating substances which are suitable for administration to mammals. The carriers should be sufficiently pure and have low toxicity to render them suitable for administration to mammals. Some examples of substances which can serve as pharmaceutical carriers are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid 5 and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, wetting agents, such sodium lauryl sulfate; coloring agents; flavoring agents; tableting agents, stabilizers; antioxidants; preservatives; pyrogen-free water; isotonic saline; phosphate buffer solutions, and the like. The choice of a pharmaceutical carrier to be used in conjunction with the subject compound is basically determined by the way the compound is to be administered.

While the present invention has been described in conjunction with specific embodiments set forth, many alternatives, modifications and variations are intended to fall within the spirit and scope of the present invention.

What is claimed is:

1. A method of treating breast cancer in mammals by administering a safe and effective amount of a pharmaceutical composition comprising compounds represented by:

Structure I

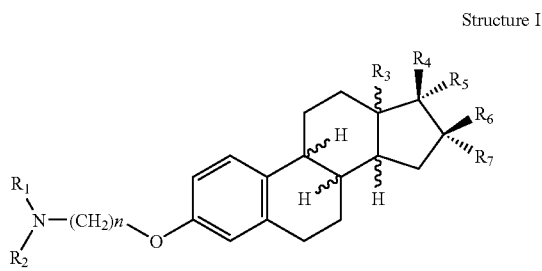

or a stereoisomer, enantiomer, rotomer, tautomer or a pharmaceutically acceptable salt thereof, wherein:
a) $R_1$ and $R_2$ are independently selected from the group consisting of hydrogen and alkyl having from 1 to 8 carbon atoms, or $R_1$ and $R_2$ taken together with nitrogen form a saturated 5 to 6 ring heterocycle,
b) $R_3$ is α or β methyl,
c) n is an integer from 2 to 10,
d) $R_4$ is selected from the group consisting of hydrogen, hydroxy, ethynyl, fluorine, chlorine, bromine, iodine and acyloxy of a organic carboxylic acid of from 1 to 10 carbon atoms and alkyl, alkenyl and alkynyl of from 1 to 10 carbons,
e) $R_5$ selected from the group consisting of hydrogen, hydroxy, fluorine, ethynyl, chlorine, bromine, iodine and acyloxy of a organic carboxylic acid of from 1 to 10 carbons atoms and alkyl, alkenyl and alkynyl of from 1 to 10 carbons,
f) $R_6$ and $R_7$ are independently selected from the group consisting of hydrogen, hydroxy, ethynyl, fluorine, chlorine, bromine, iodine and acyloxy of a organic carboxylic acid of from 1 to 10 carbons.

2. The method of claim 1, wherein $R_1$ and $R_2$ are selected from the group consisting of methyl, ethyl, isopropyl, pyrrolidinyl cyclic ring, or morpholinyl cyclic ring, or piperidinyl cyclic ring.

3. A method of treating breast cancer in mammals by administering a safe and effective amount of a pharmaceutical composition comprising compounds represented by:

Structure I

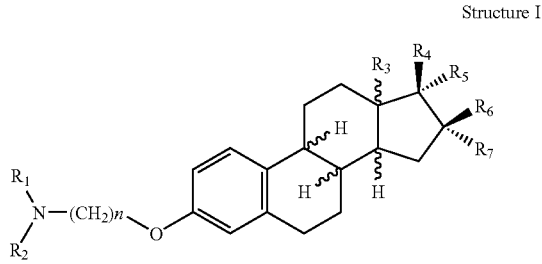

or a stereoisomer, enantiomer, rotomer, tautomer or a pharmaceutically acceptable salt thereof, wherein:
a) $R_1$ and $R_2$ are independently selected from the group consisting of hydrogen and alkyl having from 1 to 8 carbon atoms, or $R_1$ and $R_2$ taken together with nitrogen form a saturated 5 to 6 ring heterocycle,
b) $R_3$ is α or β methyl,
c) n is an integer from 2 to 10,
d) $R_4$ and $R_5$ form a double-bond with oxygen (=O) or hydroximino (=NOH), and e) $R_6$ and $R_7$ are independently selected from the group consisting of hydrogen, hydroxy, ethynyl, fluorine, chlorine, bromine, iodine and acyloxy of a organic carboxylic acid of from 1 to 10 carbons.

4. The method of claim 3, wherein $R_1$ and $R_2$ are selected from the group consisting of methyl, ethyl, isopropyl, pyrrolidinyl cyclic ring, or morpholinyl cyclic ring or -piperidinyl cyclic ring.

5. A method of treating breast cancer in mammals by administering a safe and effective amount of a pharmaceutical composition comprising compounds represented by:

Structure II

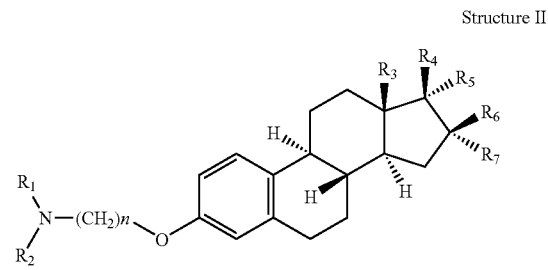

or a stereoisomer, enantiomer, rotomer, tautomer or pharmaceutically acceptable salt form thereof, wherein:
a) $R_1$ and $R_2$ are independently hydrogen, alkyl of from 1 to 8 carbon atoms, or $R_1$ and $R_2$ taken together with nitrogen form a saturated 5 to 6 ring heterocycle,
b) n is an integer of 2 to 10
c) $R_3$ is β methyl,
d) $R_4$ is hydroxy,
e) $R_5$ is hydrogen, and
f) $R_6$ and $R_7$ are hydrogen.

6. The method of claim 5, wherein $R_1$ and $R_2$ are selected from the group consisting of methyl, ethyl, isopropyl, pyrrolidinyl cyclic ring, or morpholinyl cyclic ring or a piperidinyl cyclic ring.

7. The method according to claim 5, wherein one or more of the compounds are selected from the group consisting of:
(17β)-3-[2-dimethylamino]-ethoxy]-$\Delta^{1,3,5(10)}$-estrien-17-ol,
(17β)-3-[2-diethylamino]-ethoxy]-$\Delta^{1,3,5(10)}$-estrien-17-ol,
(17β)-3-[2-diisopropylamino]-ethoxy]-]-$\Delta^{1,3,5(10)}$-estrien-17-ol,
(17β)-3-[2-morpholinyl]-ethoxy]-]-$\Delta^{1,3,5(10)}$-estrien-17-ol,
(17β)-3-[2-piperidinyl]-ethoxy]-]-$\Delta^{1,3,5(10)}$-estrien-17-ol, and
(17β)-3-[2-pyrrolidinylamino]-ethoxy]-]-$\Delta^{1,3,5(10)}$-estrien-17-ol.

8. The method according to claim 5, wherein the compound is
(17β)-3-[2-dimethylamino]-ethoxy]-$\Delta^{1,3,5(10)}$-estrien-17-ol.

9. The method according to claim 5, wherein the compound is
(17β)-3-[2-diethylamino]-ethoxy]-]-$\Delta^{1,3,5(10)}$-estrien-17-ol.

10. The method according to claim 5, wherein the compound is
(17β)-3-[2-diisopropylamino]-ethoxy]-]-$\Delta^{1,3,5(10)}$-estrien-17-ol.

11. The method according to claim 5, wherein the compound is
(17β)-3-[2-morpholinyl]-ethoxy]-]-Δ$^{1,3,5(10)}$-estrien-17-ol.

12. The method according to claim 5, wherein the compound is
(17β)-3-[2-piperidinyl]-ethoxy]-]-Δ$^{1,3,5(10)}$-estrien-17-ol.

13. The method according to claim 5, wherein the compound is
(17β)-3-[2-pyrrolidinylamino]-ethoxy]-]-Δ$^{1,3,5(10)}$-estrien-17-ol.

14. A method of treating breast cancer in mammals by administering a safe and effective amount of a pharmaceutical composition comprising compounds represented by:

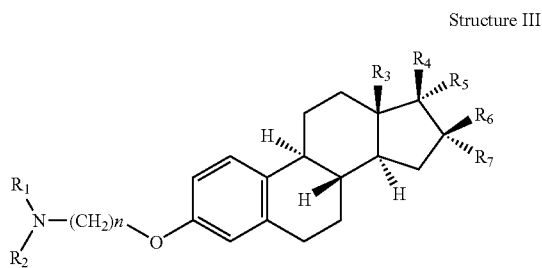

Structure III or a stereoisomer enantiomer, rotomer, tautomer or a pharmaceutically acceptable salt thereof, wherein:
a) $R_1$ and $R_2$ are independently selected from the group consisting of hydrogen alkyl having from 1 to 8 carbon atoms, or $R_1$ and $R_2$ taken together with nitrogen form a saturated 5 to 6 ring heterocycle,
b) n is an integer of from 2 to 10
c) $R_3$ is β methyl,
d) $R_4$ is hydroxy,
e) $R_5$ is ethynyl, and
f) $R_6$ and $R_7$ are hydrogen.

15. The method of claim 14, wherein $R_1$ and $R_2$ are selected from the group consisting of methyl, ethyl, isopropyl, pyrrolidinyl cyclic ring, morpholinyl cyclic ring, and a piperidinyl cyclic ring.

16. The method according to claim 14, wherein one or more of the compounds are selected from the group consisting of:
3-[2-dimethylamino]-ethoxy]-]-Δ$^{1,3,5(10)}$-estrien-17α-ethynyl-17β-ol,
3-[2-diethylamino]-ethoxy]-]-Δ$^{1,3,5(10)}$-estrien-17α-ethynyl-17β-ol,
3-[2-diisopropylamino]-ethoxy]-]-Δ$^{1,3,5(10)}$-estrien-17α-ethynyl-17β-ol,
3-[2-morpholinyl]-ethoxy]-]-Δ$^{1,3,5(10)}$-estrien-17α-ethynyl-17β-ol,
3-[2-piperidinyl]-ethoxy]-]-Δ$^{1,3,5(10)}$-estrien-17α-ethynyl-17β-ol, and
3-[2-pyrrolidinylamino]-ethoxy]-]-Δ$^{1,3,5(10)}$-estrien-17α-ethynyl-17β-ol.

17. The method according to claim 14, wherein the compound is
17β)-3-[2-dimethylamino]-ethoxy]-Δ$^{1,3,5(10)}$-estrien-17α-ethynyl-17β-ol.

18. The method according to claim 14, wherein the compound is
(17β)-3-[2-diethylamino]-ethoxy]-]-Δ$^{1,3,5(10)}$-estrien-17α-ethynyl-17β-ol.

19. The method according to claim 14, wherein the compound is
(17β)-3-[2-diisopropylamino]-ethoxy]-]-Δ$^{1,3,5(10)}$-estrien-17α-ethynyl-17β-ol.

20. The method according to claim 14, wherein the compound is
(17β)-3-[2-morpholinyl]-ethoxy]-]-Δ$^{1,3,5(10)}$-estrien-17α-ethynyl-17β-ol.

21. The method according to claim 14, wherein the compound is
(17β)-3-[2-piperidinyl]-ethoxy]-]-Δ$^{1,3,5(10)}$-estrien-17α-ethynyl-17β-ol.

22. The method according to claim 14, wherein the compound is
(17β)-3-[2-pyrrolidinylamino]-ethoxy]-]-Δ$^{1,3,5(10)}$-estrien-17α-ethynyl-17β-ol.

23. A method of treating breast cancer in mammals by administering a safe and effective amount of a pharmaceutical composition comprising compounds represented by:

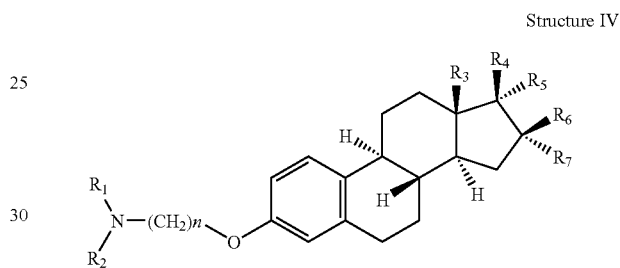

Structure IV

Wherein:
a) $R_1$ and $R_2$ are independently selected from the group consisting of hydrogen alkyl having from 1 to 8 carbon atoms, or $R_1$ and $R_2$ taken together with nitrogen form a saturated 5 to 6 ring heterocycle,
b) n is an integer of from 2 to 10,
c) $R_3$ is β methyl,
d) $R_4$ and $R_5$ form a double-bond with oxygen (═O), and
e) $R_6$ and $R_7$ are hydrogen.

24. The method of claim 23 wherein $R_1$ and $R_2$ are selected from the group consisting of methyl, ethyl, isopropyl, pyrrolidinyl cyclic ring, morpholinyl cyclic ring and a piperidinyl cyclic ring.

25. The method according to claim 23, wherein one or more of the compounds are selected from the group consisting of:
3-[2-dimethylamino]-ethoxy]-]-Δ$^{1,3,5(10)}$-estrien-17-one,
3-[2-diethylamino]-ethoxy]-]-Δ$^{1,3,5(10)}$-estrien-17-one,
3-[2-diisopropylamino]-ethoxy]-]-Δ$^{1,3,5(10)}$-estrien-17-one,
3-[2-morpholinyl]-ethoxy]-]-Δ$^{1,3,5(10)}$-estrien-17-one,
3-[2-piperidinyl]-ethoxy]-]-Δ$^{1,3,5(10)}$-estrien-17-one, and
3-[2-pyrrolidinylamino]-ethoxy]-]-Δ$^{1,3,5(10)}$-estrien-17-one.

26. The method according to claim 23, wherein the compound is
17β)-3-[2-dimethylamino]-ethoxy]-Δ$^{1,3,5(10)}$-estrien-17-one.

27. The method according to claim 23, wherein the compound is
(17β)-3-[2-diethylamino]-ethoxy]-]-Δ$^{1,3,5(10)}$-estrien-17-one.

28. The method according to claim 23, wherein the compound is (17β)-3-[2-diisopropylamino]-ethoxy]-]-$\Delta^{1,3,5(10)}$-estrien-17-one.

29. The method according to claim 23, wherein the compound is (17β)-3-[2-morpholinyl]-ethoxy]-]-$\Delta^{1,3,5(10)}$-estrien-17-one.

30. The method according to claim 23, wherein the compound is (17β)-3-[2-piperidinyl]-ethoxy]-]-$\Delta^{1,3,5(10)}$-estrien-17-one.

31. The method according to claim 23, wherein the compound is (17β)-3-[2-pyrrolidinylamino]-ethoxy]-]-$\Delta^{1,3,5(10)}$-estrien-17-one.

* * * * *

UNITED STATES PATENT AND TRADEMARK OFFICE
CERTIFICATE OF CORRECTION

PATENT NO.         : 7,687,486 B2
APPLICATION NO.    : 11/073087
DATED              : March 30, 2010
INVENTOR(S)        : John S. Cooperwood Page 1 of 1

It is certified that error appears in the above-identified patent and that said Letters Patent is hereby corrected as shown below:

In the Specification

Column 1, line 6, please amend as follows:

This invention was made with government support under G12 RR 03020 which was awarded by the National Institutes of Health. The government has certain rights in the invention.

Signed and Sealed this
Twenty-seventh Day of October, 2015

Michelle K. Lee
*Director of the United States Patent and Trademark Office*